US00PP35123P2

(12) United States Plant Patent
Wood

(10) Patent No.: US PP35,123 P2
(45) Date of Patent: Apr. 25, 2023

(54) ***SYRINGA* PLANT NAMED 'SMNSPTP'**

(50) Latin Name: *Syringa pubescens*
Varietal Denomination: SMNSPTP

(71) Applicant: Timothy D. Wood, Spring Lake, MI (US)

(72) Inventor: Timothy D. Wood, Spring Lake, MI (US)

(73) Assignee: SPRING MEADOW NURSERY INC., Grand Haven, MI (US)

( * ) Notice: Subject to any disclaimer, the term of this patent is extended or adjusted under 35 U.S.C. 154(b) by 0 days.

(21) Appl. No.: 17/953,200

(22) Filed: Sep. 26, 2022

(51) Int. Cl.
*A01H 6/00* (2018.01)
*A01H 5/02* (2018.01)

(52) U.S. Cl.
USPC ..... Plt./248

(58) Field of Classification Search
USPC ..... Plt./248
CPC ..... A01H 6/00; A01H 5/00
See application file for complete search history.

*Primary Examiner* — Keith O. Robinson
(74) *Attorney, Agent, or Firm* — C. Anne Whealy

(57) ABSTRACT

A new and distinct cultivar of *Syringa* plant named 'SMNSPTP', characterized by its relatively compact, upright to outwardly spreading and mounding plant habit; moderately vigorous growth habit; freely branching habit; freely and remontant flowering habit; large inflorescences with fragrant light purple-colored flowers and dark purplish red-colored flower buds; and good garden performance.

2 Drawing Sheets

Figure 1:
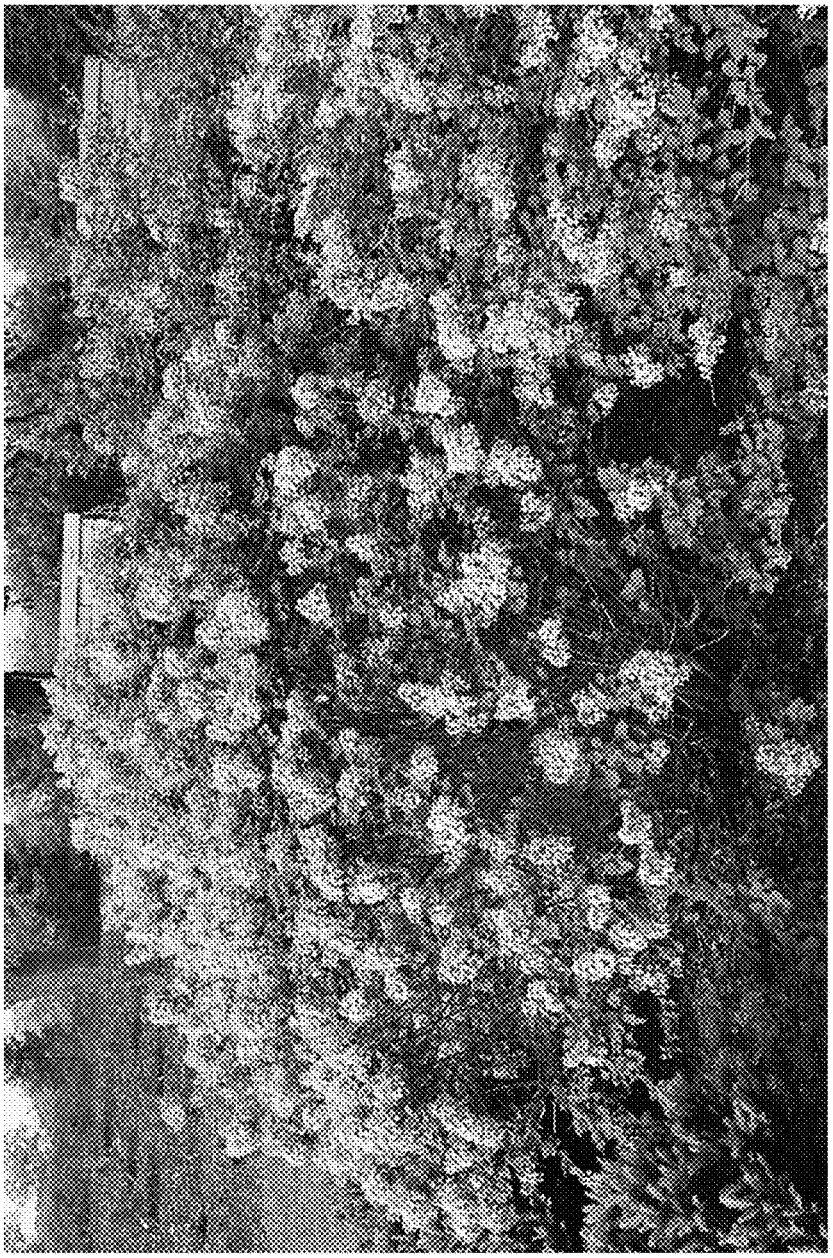

Botanical designation: *Syringa pubescens.*
Cultivar denomination: 'SMNSPTP'.

BACKGROUND OF THE INVENTION

The present invention relates to a new and distinct cultivar of *Syringa* plant, commonly referred to as Lilac, botanically known as *Syringa pubescens* and hereinafter referred to by the name 'SMNSPTP'.

The new *Syringa* plant is plant is a product of a planned breeding program conducted by the Inventor in Grand Haven, Mich. The objective of the breeding program is to create new compact and freely-flowering *Syringa* plants with attractive flowers and remontant flowering habit.

The new *Syringa* plant originated from a cross-pollination in 2011 of a proprietary selection of *Syringa pubescens* with the code designation BigPur, not patented, as the female, or seed, parent with a proprietary selection of *Syringa pubescens* with the code designation PkTruss, not patented, as the male, or pollen, parent. The new *Syringa* plant was discovered and selected by the Inventor in 2014 as a single flowering plant within the progeny of the stated cross-pollination in a controlled environment in Grand Haven, Mich.

Asexual reproduction of the new *Syringa* plant by softwood to semi-hardwood cuttings in a controlled greenhouse environment in Grand Haven, Mich. since 2014 has shown that the unique features of this new *Syringa* plant are stable and reproduced true to type in successive generations of asexual reproduction.

SUMMARY OF THE INVENTION

Plants of the new *Syringa* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SMNSPTP'. These characteristics in combination distinguish 'SMNSPTP' as a new and distinct *Syringa* plant:

1. Relatively compact, upright to outwardly spreading and mounding plant habit.
2. Moderately vigorous growth habit.
3. Freely branching habit.
4. Freely and remontant flowering habit.
5. Large inflorescences with fragrant light purple-colored flowers and dark purplish red-colored flower buds.
6. Good garden performance.

Plants of the new *Syringa* can be compared to plants of the female and male selection parents. Plants of the new *Syringa* differ primarily from plants of the female and male parent selections in flowering habit as plants of the new *Syringa* are more freely flowering and flower more remontantly than plants of the female and male parent selections.

Plants of the new *Syringa* can be compared to plants of the *Syringa hybrida* 'SMNJRPU', disclosed in U.S. Plant Pat. No. 29,831. In side-by-side comparisons, plants of the new *Syringa* differ primarily from plants of 'SMNJRPU' in the following characteristics:

1. Plants of the new *Syringa* have larger and denser inflorescences than plants of 'SMNJRPU'.
2. Flowers of plants of the new *Syringa* are lighter purple in color than flowers of plants of 'SMNJRPU'.

BRIEF DESCRIPTION OF THE PHOTOGRAPHS

The accompanying colored photographs illustrate the overall appearance of the new *Syringa* plant showing the colors as true as it is reasonably possible to obtain in colored reproductions of this type. Colors in the photographs may differ slightly from the color values cited in the detailed botanical description which accurately describe the colors of the new *Syringa* plant.

The photograph on the first sheet (FIG. 1) is a side perspective view of typical flowering plants of 'SMNSPTP' grown in an outdoor nursery.

Figure 2:
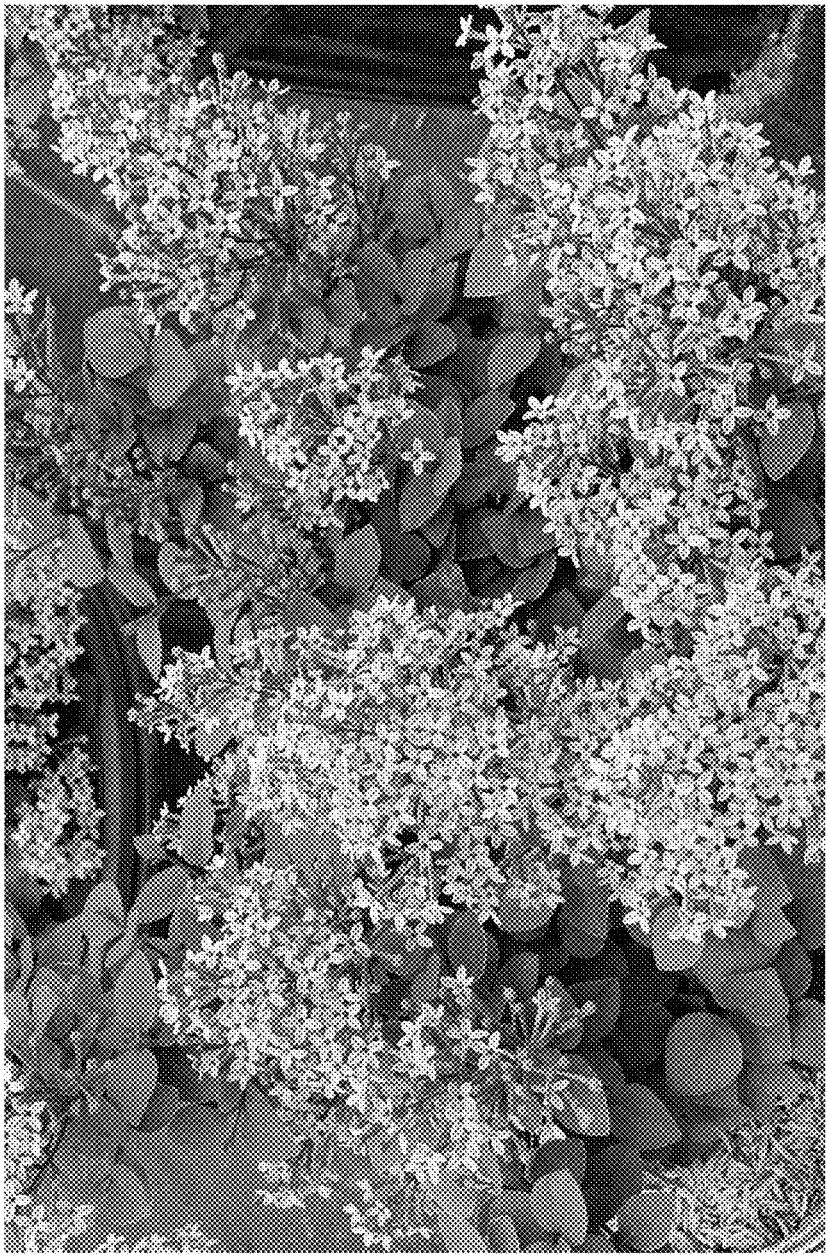

The photograph on the second sheet (FIG. 2) is a close-up view of a typical flowering typical plant of 'SMNSPTP'.

DETAILED BOTANICAL DESCRIPTION

Plants used for the following description were grown during the spring in three-gallon containers in a polyethylene-covered greenhouse and in an outdoor nursery in Grand Haven, Mich. and under cultural practices typical of commercial *Syringa* production. During the production of the plants, day temperatures ranged from 18° C. to 27° C. and night temperatures ranged from 5° C. to 10° C. Plants of the new *Syringa* were three years old when the photographs and description were taken. In the following description, color references are made to The Royal Horticultural Society Colour Chart, 2015 Edition, except where general terms of ordinary dictionary significance are used.

Botanical classification: *Syringa pubescens* 'SMNSPTP'.

Parentage:

- *Female, or seed, parent*.—Proprietary selection of *Syringa pubescens* with the code designation BigPur, not patented.
- *Male, or pollen, parent*.—Proprietary selection of *Syringa pubescens* with the code designation PkTruss, not patented.

Propagation:

- *Type*.—By softwood cuttings.
- *Time to initiate roots, summer*.—About 20 days at temperatures about 18° C. to 27° C.
- *Time to produce a rooted young plant, summer*.—About three months at temperatures about 18° C. to 27° C.
- *Root description*.—Fine, fibrous; typically white in color, actual color of the roots is dependent on substrate composition, water quality, fertilizer, substrate temperature and physiological age of roots.
- *Rooting habit*.—Freely branching; dense.

Plant description:

- *Plant form and growth habit*.—Perennial shrub; relatively compact, upright to outwardly spreading and mounding plant habit; moderately vigorous growth habit and moderate growth rate.
- *Branching habit*.—Freely branching habit, about 30 lateral branches develop per plant.
- *Plant height*.—About 45 cm.
- *Plant diameter* (*area of spread*).—About 55 cm.

Lateral branch description:

- *Length*.—About 35 cm.
- *Diameter*.—About 6 mm.
- *Internode length*.—About 3 cm.
- *Aspect*.—About 45° to 80° from vertical.
- *Strength*.—Strong.
- *Texture*.—Initially slightly pubescent becoming smooth and glabrous with development.
- *Color, developing*.—Close to 144B.
- *Color, developed*.—Close to 199B.

Leaf description:

- *Arrangement*.—Opposite, simple.
- *Length*.—About 2 cm.
- *Width*.—About 1.75 cm.
- *Shape*.—Ovate.
- *Apex*.—Acute.
- *Base*.—Obtuse.
- *Margin*.—Entire.
- *Texture, upper and lower surfaces*.—Pubescent, velvety.
- *Venation pattern*.—Pinnate.
- *Color*.—Developing and fully expanded leaves, upper surface: Close to NN137B; venation, close to NN137B. Developing and fully expanded leaves, lower surface: Close to 147B; venation, close to NN137B.
- *Petioles*.—Length: About 4 mm. Diameter: About 1 mm. Texture, upper and lower surfaces: Pubescent. Color, upper and lower surfaces: Close to NN137B tinged with close to 177A.

Flower description:

- *Flower arrangement and flowering habit*.—Single salverform flowers arranged in dense terminal panicles; freely flowering habit with usually about 500 to 700 flowers developing per inflorescence; flowers face upright to mostly outwardly depending on position on inflorescence.
- *Natural flowering season and flower longevity*.—Plants of the new *Syringa* flower during the spring and summer in Michigan; flowering remontant; flowers not persistent.
- *Fragrance*.—Strongly fragrant; fragrance sweet, floral and pleasant.
- *Inflorescence height*.—About 10 cm.
- *Inflorescence diameter*.—About 8.5 cm.
- *Flower diameter*.—About 8 mm.
- *Flower depth*.—About 1.25 cm.
- *Flower throat diameter*.—About 1.5 mm.
- *Flower tube length*.—About 1.25 mm.
- *Flower tube diameter, proximally*.—About 1 mm.
- *Flower buds*.—Length: About 7 mm. Diameter: About 2 mm. Shape: Proximally, oblong and distally, orbicular. Color: Close to 71A.
- *Petals*.—Quantity and arrangement: Single whorl of four petals; lower portion of petals fused forming a narrow tube. Lobe length: About 3 mm. Lobe width: About 2 mm. Lobe shape: Elliptic. Apex: Acute. Margin: Entire. Texture, upper and lower surfaces: Smooth, glabrous; soft. Texture, throat and tube: Smooth, glabrous. Color: When opening and fully opened, upper surface: Close to N75A and towards the margins, close to 76B; color does not change with subsequent development. When opening and fully opened, lower surface: Close to 76B; color does not change with subsequent development. Throat: Close to 76B. Tube: Close to 76B.
- *Sepals*.—Quantity and arrangement: Single whorl of four small sepals; fused towards the base forming a campanulate-shaped calyx. Length: Less than 1 mm. Width: Less than 1 mm. Shape: Narrowly deltoid. Apex: Acute. Margin: Entire. Texture, upper and lower surfaces: Smooth, glabrous. Color, upper and lower surfaces: Close to 71A.
- *Peduncles*.—Length: About 7 cm. Diameter: About 3 mm. Strength: Strong; somewhat flexible. Aspect: About 90° from the stem axis. Texture: Pubescent. Color: Close to 177A.

*Pedicels*.—Length: About 7 mm. Diameter: About 1 mm. Strength: Strong; flexible. Aspect: About 45° from peduncle axis. Texture: Pubescent. Color: Close to 177A.

*Reproductive organs*.—Androecium: Quantity of stamens per flower: Two; filaments are adnate to the throat. Anther length: About 2 mm. Anther shape: Oblong. Anther color: Close to 160A. Amount of pollen: Moderate. Pollen color: Close to 160A. Gynoecium: Quantity of pistils per flower: One. Pistil length: About 3 mm. Style length: About 2 mm. Style color: Close to 76B. Stigma shape: Oblong to rounded. Stigma color: Close to 160C.

*Seeds and fruits*.—To date, seed and fruit development have not been observed on plants of the new *Syringa*.

Garden performance: Plants of the new *Syringa* have been observed to have good garden performance and to tolerate rain, wind and temperatures ranging from about −31° C. to about 38° C.

Pathogen & pest resistance: To date, plants of the new *Syringa* have not been observed to be resistant to pathogens and pests common to *Syringa* plants.

It is claimed:

1. A new and distinct *Syringa* plant named 'SMNSPTP' as illustrated and described.

* * * * *